US012710411B2

(12) United States Patent
Takada

(10) Patent No.: US 12,710,411 B2
(45) Date of Patent: Aug. 18, 2026

(54) GAS SENSOR FOR DETECTING VOLATILE ORGANIC COMPOUNDS AND METHOD FOR MANUFACTURING SAME

(71) Applicant: LG ELECTRONICS INC., Seoul (KR)

(72) Inventor: Masaki Takada, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 587 days.

(21) Appl. No.: 18/202,791

(22) Filed: May 26, 2023

(65) Prior Publication Data

US 2024/0393306 A1 Nov. 28, 2024

(51) Int. Cl.
*G01N 33/00* (2006.01)
*B01L 3/00* (2006.01)

(52) U.S. Cl.
CPC ........ *G01N 33/0047* (2013.01); *B01L 3/5023* (2013.01); *B01L 2300/0645* (2013.01); *B01L 2300/069* (2013.01)

(58) Field of Classification Search
CPC .... G01N 33/0047; G01N 33/20; G01N 27/00; G01N 27/5438; G01N 27/04; G01N 27/22; B01L 3/5023; B01L 2300/0645; B01L 2300/069; Y10T 436/25875
USPC ....... 422/82.01, 82.02, 82.03, 82.04, 83, 88, 422/90, 98; 436/73, 77, 79, 149, 181
See application file for complete search history.

(56) References Cited

U.S. PATENT DOCUMENTS 12,196,698 B2 * 1/2025 Ishikura ............... G01N 27/127
2013/0111974 A1 * 5/2013 Barsan ................. G01N 27/125 73/23.2
2022/0155247 A1 * 5/2022 Park ....................... C01G 19/02
2024/0085369 A1 * 3/2024 Chang ................ G01N 33/4975
(Continued)

FOREIGN PATENT DOCUMENTS

CN 102680540-8 6/2014
JP 10-185849 A 7/1998
JP 11-83774 A 3/1999
(Continued)

OTHER PUBLICATIONS

Ling et al., "Influence of nano-scale dopants of Pt, CaO and SiO2, on the alcohol sensing of SnO2 thin films", Sensors and Actuators B, vol. 119, 2006, pp. 497-503.
(Continued)

*Primary Examiner* — Maureen Wallenhorst
(74) *Attorney, Agent, or Firm* — Birch, Stewart, Kolasch & Birch, LLP

(57) ABSTRACT

Discussed is a gas sensor for detecting volatile organic compounds, the gas sensor including a substrate including a non-conductive material, an electrode located on the substrate and including a conductive material, and a sensing layer configured to be in contact with at least a portion of the electrode or to cover the electrode, the sensing layer reacting to a predetermined gas, wherein the sensing layer includes a compound of $SnO_2$ with an alkali metal oxide or an alkaline earth metal oxide. The sensing layer specifically reacts to formaldehyde among volatile organic compounds. When the sensing layer detects formaldehyde by connecting electrodes to each other, the sensing layer can detect the formaldehyde by checking a change in current in the electrode.

16 Claims, 4 Drawing Sheets

(56) References Cited

U.S. PATENT DOCUMENTS

2024/0353383 A1 * 10/2024 Curtin ................ G01N 33/0031

FOREIGN PATENT DOCUMENTS

| | | | | |
|---|---|---|---|---|
| JP | 3503154 | B2 | | 8/2006 |
| JP | 3803154 | B2 | * | 8/2006 |
| JP | 2007-139669 | A | | 6/2007 |
| JP | 2010-91501 | A | | 4/2010 |
| JP | 2010-133926 | A | | 6/2010 |
| JP | 2022-526947 | A | | 5/2022 |
| KR | 10-2181598 | B1 | | 11/2020 |
| WO | WO 2017/067865 | A1 | | 4/2017 |
| WO | WO 2022/136847 | A1 | | 6/2022 |
| WO | 2024/232480 | A1 | * | 11/2024 |

OTHER PUBLICATIONS

Min et al., “Undoped and 0.1 wt. % Ca-doped Pt-catalyzed SnO2 sensors for CH4 detection”, Sensors and Actuators B, vol. 108, 2005, pp. 119-124.

* cited by examiner

-- PRIOR ART --

GAS SENSOR FOR DETECTING VOLATILE ORGANIC COMPOUNDS AND METHOD FOR MANUFACTURING SAME

BACKGROUND OF THE DISCLOSURE

Field

The present disclosure relates generally to a gas sensor for detecting volatile organic compounds. More particularly, the present disclosure relates to a gas sensor capable of specifically detecting formaldehyde among volatile organic compounds and a method for manufacturing the same.

Discussion of the Related Art

Physical disorders such as sore eyes, headaches, and allergies can occur indoors immediately after new construction or renovation. This is called a sick building syndrome, and the cause is known to be volatile organic compounds (VOC), primarily, formaldehyde.

Among volatile organic compounds, formaldehyde is contained in various adhesives, flooring materials, and particle board or plywood, and is released when these are used in indoor spaces, causing problems. It is impossible to completely avoid use of these things, and when volatile organic compounds including formaldehyde are generated therefrom, the volatile organic compounds have many adverse effects on indoor residents.

Looking at the effect of formaldehyde on the human body, when concentration of formaldehyde in the air is about 0.04 ppm, nervous tissues begin to be stimulated, and sensitive children can develop atopic dermatitis. When the concentration of formaldehyde is 0.05 to 1.0 ppm, it can be smelled, and this level of the concentration is an indoor standard in Canada and California. When concentration of formaldehyde in the air is 0.2 ppm, eye irritation begins, and when the concentration is 0.25 to 0.33 ppm, a respiratory failure can occur. The concentration of 0.5 ppm is the lowest level at which stimulation of the throat begins and is the highest level allowed by the Korean Society of Industrial Hygiene. When the concentration is 2.0 to 3.0 ppm, pain in the eyes begins, and when the concentration is 4.0 ppm, tearing can occur. When the concentration is 10.0 to 20.0 ppm, intense tearing and difficulty in breathing can occur, and when the concentration is 30.0 ppm or more, acute poisoning can occur within minutes and death can occur from toxic emphysema.

For reference, in the indoor environmental standards set by the World Health Organization (WHO) and Japan, the concentration of formaldehyde in the air is 0.08 ppm. In accordance with these standards, it is necessary to detect the concentration of formaldehyde in the air by using a gas sensor.

However, when formaldehyde is generated, other volatile organic compound (VOC) gases such as alcohol can exist. However, since general volatile organic compounds and formaldehyde have different effects on the human body, the specific and selective sensitivity of the gas sensor to formaldehyde is required.

A general gas sensor has similar sensitivity to most volatile organic compounds, and such an example can be seen in Japanese Patent No. 3854358. Here, electrodes made of gold (Au) are formed on a substrate, and tin oxide ($SnO_2$) to which at least one element of Ga, Y, La, and Nd is added is used as a sensing material between the electrodes.

However, such a gas sensor of a prior art has similar sensitivity to most volatile organic compounds. For example, when using a sensing material in which Pd or Gd is added to $SiO_2$, the sensitivity S of the gas sensor to 0.1 ppm of formaldehyde is 20%, but the sensitivity S of the gas sensor to 1 ppm of volatile organic compounds also is 25%. The sensitivity is obtained by converting the percentage of a resistance change. Accordingly, the gas sensor of the prior art detects both formaldehyde and volatile organic compounds with high sensitivity, but cannot selectively detect only formaldehyde.

FIG. 1 illustrates the responsiveness of the gas sensor of the prior art. This is provided in a paper titled "Study on a micro-gas sensor with $SnO_2$—NiO sensitive film for indoor formaldehyde detection" (Sensors and Actuators B vol. 132, ((2008) p74~80). Here, the gas sensor is a MEMS structure using $SnO_2$—NiO as a sensing material and using Pt in an electrode to detect formaldehyde.

However, the gas sensor in this paper has a sensitivity S of 0.06 ppm of formaldehyde which is 1.6% and a sensitivity S of 1 ppm of ethanol which is 0.1% or less. Furthermore, the sensitivity ratio of formaldehyde to ethanol is greater than 10, and the interference of the ethanol gas is suppressed. However, the sensitivity S of formaldehyde is 1.6%, which is very low.

In other words, the gas sensor is more sensitive to formaldehyde than volatile organic compounds including alcohol, but has a fundamental limitation in that the gas sensor cannot selectively detect formaldehyde.

Accordingly, the gas sensor of the prior art detects the presence of volatile organic compounds, but has a problem in that the gas sensor cannot provide information on whether formaldehyde is included in the volatile organic compounds and if included, how much formaldehyde is included therein.

SUMMARY OF THE DISCLOSURE

An objective of the present disclosure is to provide a gas sensor with the highest sensitivity to formaldehyde in volatile organic compounds.

Another objective of the present disclosure is to provide a gas sensor capable of detecting the presence or concentration of formaldehyde among volatile organic compounds.

Still another objective of the present disclosure is to provide a gas sensor that maintains both high sensitivity and high selectivity.

According to the present disclosure, there is provided a gas sensor including a novel combination of sensing materials including an alkali metal element or an alkaline earth metal element and having high sensitivity and high selectivity.

According to the present disclosure, formaldehyde can be detected by forming a sensing layer by using a compound of a $SnO_2$ with an alkali metal oxide or an alkaline earth metal oxide.

According to the present disclosure, the gas sensor is configured to have an electrode including an indium tin oxide (ITO).

The gas sensor of the present disclosure includes: a substrate made of a non-conductive material; the electrode located on the substrate and formed of a conductive material; and the sensing layer configured to be in contact with at least a portion of the electrode or to cover the electrode, the sensing layer reacting to gas, wherein the sensing layer can include a compound of $SnO_2$ with an alkali metal oxide or an alkaline earth metal oxide.

The alkali metal oxide can include at least one element of Li, Na, K, Rb, Cs, and Fr.

The alkaline earth metal oxide can include at least one element of Be, Mg, Ca, Sr, Ba, and Ra.

The electrode can be formed of an indium tin oxide (ITO).

The electrode can include a first electrode formed on the substrate, and a second electrode formed on the substrate by being spaced apart from the first electrode, and the sensing layer can be disposed to connect the first electrode with the second electrode.

The sensing layer can be configured to expose at least a portion of each of the first electrode and the second electrode to the air.

A heater can be provided on the substrate, the heater being located on a surface of the substrate on which the electrode is located or on a surface opposite to the surface of the substrate on which the electrode is located.

The gas sensor of the present disclosure includes: the substrate made of a non-conductive material; the sensing layer located on the substrate; and the electrode made of a conductive material and configured to detect electron movement and capacitance inside the sensing layer, wherein the electrode can include the first electrode formed of a conductive material, and the second electrode configured to supply an electric current to the first electrode or to receive an electric current from the first electrode, and the sensing layer can connect the first electrode with the second electrode and can be configured to expose at least a portion of each of the first electrode and the second electrode to the air.

The sensing layer can be disposed between the substrate and the electrode.

The first electrode and the second electrode can be provided on an outer surface of the sensing layer.

The sensing layer can shield a portion of the first electrode and a portion of the second electrode.

The heater can be provided on the substrate, the heater being located on the surface of the substrate on which the electrode is located or on the surface opposite to the surface of the substrate on which the electrode is located.

According to the present disclosure, a method for manufacturing a gas sensor for detecting volatile organic compounds, with the gas sensor having the sensing layer configured to connect electrodes to each other formed on a substrate, includes: forming the electrodes by using an indium tin oxide (ITO), and forming the sensing layer by using the compound of $SnO_2$ with an alkali metal oxide or an alkaline earth metal oxide.

The alkali metal oxide can include at least one element of Li, Na, K, Rb, Cs, and Fr, and the alkaline earth metal oxide can include at least one element of Be, Mg, Ca, Sr, Ba, and Ra.

The sensing layer can be formed by dispersing and applying Mg—$SnO_2$ onto a mixed solution of pure water and glycerin and heating the mixed solution, onto which the Mg—$SnO_2$ is applied, to a predetermined temperature.

The gas sensor of the present disclosure can have at least one of the following effects.

According to the present disclosure, formaldehyde gas at a low concentration of 10 ppb can be detected.

According to the present disclosure, the interference of other gases with formaldehyde can be avoided. Accordingly, only formaldehyde can be effectively detected.

In the gas sensor of the present disclosure, 1 ppm of ethanol gas, which is a representative volatile organic compound, has sensitivity corresponding to 10 ppb of formaldehyde or less. Accordingly, the gas sensor of the present disclosure can detect formaldehyde better than other volatile organic compounds, thereby having high selectivity to formaldehyde.

BRIEF DESCRIPTION OF THE DRAWINGS

The present invention will become more fully understood from the detailed description given hereinbelow and the accompanying drawings which are given by way of illustration only, and thus are not limitative of the present invention.

DETAILED DESCRIPTION OF THE EMBODIMENTS

Figure 1:
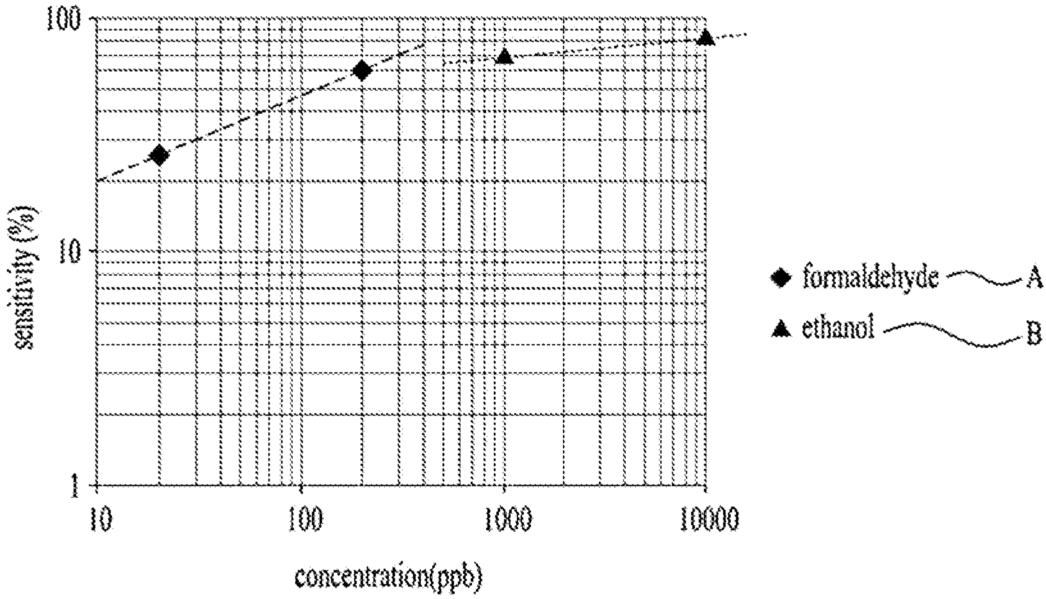
FIG. 1 is a graph illustrating that the selectivity of formaldehyde is lower than that of ethanol in a gas sensor of a prior art.

Hereinafter, embodiments disclosed in this specification will be described in detail with reference to the accompanying drawings. In this specification, the same or similar reference numerals are given to the same or similar components even in different embodiments, and the description thereof is replaced with the first description. Singular expressions used in this specification include plural expressions unless the context clearly dictates otherwise. In addition, in describing the embodiments disclosed in this specification, when it is determined that a detailed description of related known technologies can obscure the gist of the embodiments disclosed in this specification, the detailed description thereof will be omitted. In addition, it should be noted that the accompanying drawings are only for easy understanding of the embodiments disclosed in this specification, and should not be construed as limiting the technical idea disclosed in this specification by the accompanying drawings.

Figure 2:
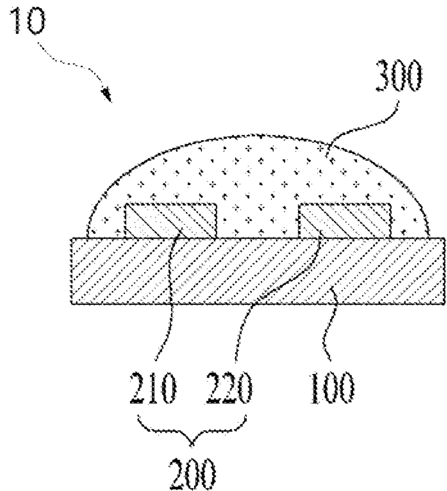
FIG. 2 is a schematic cross-sectional view illustrating the structure of a gas sensor of the present disclosure according to an embodiment.

FIG. 2 schematically illustrates the structure of the gas sensor according to an embodiment of the present disclosure. The gas sensor 10 according to the embodiment of the present disclosure has a substrate 100 constituting a frame thereof. Electrodes 200 can be located on the substrate 100. A sensing layer 300 can be provided to connect each of the electrodes 200 to each other.

The substrate 100 can be made of or include a non-conductive material such as silicon dioxide ($SiO_2$). The substrate 100 made of or including a resin-based material serves to support the electrode 200 and the sensing layer 300. The substrate 100 can be a plate having a predetermined shape. A glass substrate or an alumina substrate can be used as the substrate 100.

The electrode 200 can include at least one pair of a first electrode 210 and a second electrode 220. The first electrode 210 and the second electrode 220 can be electrically connected to the outside. The first electrode 210 and the second electrode 220 can be formed at a predetermined interval on the substrate 100, and an electric current can be transmitted between the first electrode 210 and the second electrode 220 through the sensing layer 300.

The gas sensor 10 of the present disclosure can detect formaldehyde by detecting an electric current flowing between the first electrode 210 and the second electrode 220, change in the electric current, or a change in electrical resistance or capacitance of the electrode 200.

The sensing layer 300 can be formed to cover the first electrode 210 and the second electrode 220. The sensing layer 300 can change the intensity of an electric current flowing between the first electrode 210 and the second electrode 220, or the capacitance or electrical resistance of the electrode 200. For example, a material forming the sensing layer 300 has inherent resistance, but the sensing layer 300 can have electrical properties changed when the sensing layer 300 contacts or is combined with formaldehyde.

For example, when a material of which the sensing layer 300 is formed comes into contact with or is combined with formaldehyde, the material can transfer electrons to the electrode 200 or receive electrons from the electrode 200 while causing an oxidation-reduction reaction with the formaldehyde. Alternatively, when a material of which the sensing layer 300 is formed comes into contact with or is combined with formaldehyde, the molecular arrangement structure of the sensing layer 300 can be changed due to the permeation of the formaldehyde, and thus the total charge capacity of the sensing layer 300 can be changed.

However, the sensing layer 300 need not react to other volatile organic compounds other than formaldehyde or can have a very low reactivity thereto compared to formaldehyde.

According to these characteristics, the gas sensor 10 of the present disclosure can specifically detect formaldehyde. This is because the sensing layer 300 does not react or has very low reactivity to volatile organic compounds other than formaldehyde even when the formaldehyde exists along with the volatile organic compounds in the air or indoors.

The gas sensor 10 of the present disclosure can specifically react to formaldehyde to detect formaldehyde, and need not react to other volatile organic compounds. Accordingly, hereinafter, the characteristics of the gas sensor 10 of the present disclosure not detecting other volatile organic compounds or having a low sensitivity to the other volatile organic compounds will be described.

In the gas sensor 10 of the present disclosure, materials of the electrode 200 and the sensing layer 300 are specified. For example, the materials of the electrode 200 and the sensing layer 300 are required to, or can react specifically to formaldehyde or have a significantly greater sensitivity to formaldehyde than other volatile organic compounds.

When the material of the sensing layer 300 of the present disclosure is a compound of a tin oxide ($SnO_2$) with an oxide of an alkali metal element or an oxide of an alkaline earth metal element, the sensing layer 300 has a significantly greater sensitivity to formaldehyde than to other volatile organic compounds, or reacts specifically only to the formaldehyde.

Accordingly, as the material of the sensing layer 300 of the gas sensor 10 of the present disclosure, the compound of a tin oxide ($SnO_2$) with the oxide of an alkali metal element or the oxide of an alkaline earth metal element can be selected.

The alkali metal element can include at least one element of Li, Na, K, Rb, Cs, and Fr. In addition, the alkaline earth metal element can include at least one element of Be, Mg, Ca, Sr, Ba, and Ra.

Figure 3:
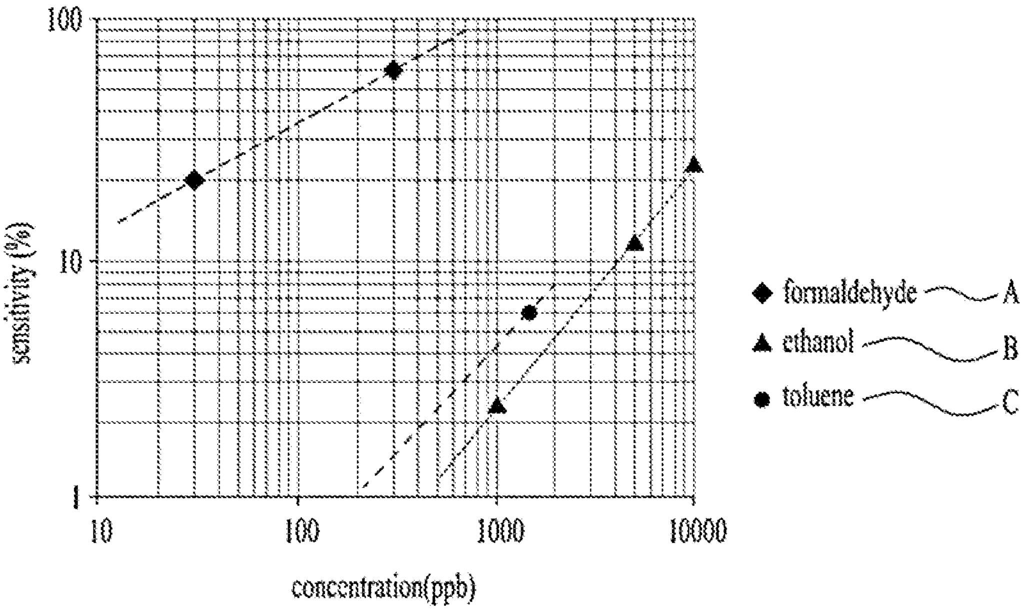
FIG. 3 is a graph illustrating the sensitivity of the gas sensor of the present disclosure to formaldehyde, ethanol, and toluene.

When Mg—$SnO_2$ is used as the material of the sensing layer 300 of the present disclosure, the sensitivity of the sensing layer 300 to ethanol, toluene, and formaldehyde is shown graphically in FIG. 3. Referring to FIG. 3, it can be seen that the sensing layer 300 has a much higher sensitivity to formaldehyde A than to ethanol B and toluene C, which react most competitively with formaldehyde A among volatile organic compounds.

For example, it can be seen that the sensitivity of the gas sensor 10 of the present disclosure to formaldehyde A is between 20% and 70%, and ethanol B and toluene C are less than 10% or only exceed 10% in most or maximum concentrations.

In addition, it can be seen that the sensitivity of the gas sensor 10 of the present disclosure is 20% or more even when the concentration of formaldehyde A is less than 100 ppb, but the sensitivity of the gas sensor 10 does not exceed 20% even when the concentration of each of ethanol B and toluene C is 1000 ppb or more.

When the sensing layer 300 is made of or includes Mg—$SnO_2$ and the electrode 200 is made of or includes ITO, which will be described later, the sensitivity of the gas sensor 10 to formaldehyde A is 20 to 60% when the concentration of the formaldehyde A is 0.03 ppm to 0.30 ppm.

However, the sensitivity of the gas sensor 10 of the present disclosure to a concentration of ethanol B of 1 ppm is 2.3%, which is very low. The sensitivity corresponds to the sensitivity of the gas sensor 10 to formaldehyde of 0.01 ppm or less.

The sensitivity of the gas sensor 10 of the present disclosure to the concentration of toluene C of 1.5 ppm is measured to be 6.8%, but the sensitivity corresponds to the concentration of formaldehyde of 0.01 ppm or less.

As a result, the gas sensor 10 of the present disclosure can detect, for example, formaldehyde A of a concentration near the concentration of 0.08 ppm, which is the environmental standard of the International Health Organization, with high sensitivity. In addition, it can be seen that the gas sensor 10 of the present disclosure measures a volatile organic compound including ethanol B or toluene C with sensitivity to the concentration of 0.01 ppm or less based on formaldehyde, and has selectivity to formaldehyde.

In the gas sensor 10 of the present disclosure, the sensing layer 300 can be made of, or include the compound of $SnO_2$ with an oxide of an alkali metal element or an oxide of an alkaline earth metal element and can specifically detect formaldehyde A.

Meanwhile, in the gas sensor 10 of the present disclosure, other metal elements need not be applied to make the sensing layer 300. This is because it is a well-known fact that the gas sensors of a prior art apply several different metal elements as a sensing material, and thus do not have the effect of specifically detecting formaldehyde, but only detect the presence of most volatile organic compounds as a whole and concentration thereof.

Additionally, when a metal other than alkali metals or alkaline earth metals is experimentally used as a material for the sensing layer 300, it is not possible to obtain an experimental result that the sensing layer 300 specifically reacts only to formaldehyde or has a higher sensitivity to formaldehyde than ethanol or toluene as illustrated in FIG. 3.

In addition, the gas sensor 10 of the present disclosure can exclude nickel and nickel oxides from the alkali metal element. In the detection sensor of the prior art used in FIG. 1, a compound of NiO and $SnO_2$ is used as a material for the sensing layer. Specifically, in the detection sensor of the prior art, $SnO_2$—NiO is used as a material of the sensing layer, and gold (Au) is used as a material of the electrode. As illustrated in FIG. 1, when formaldehyde is 0.03 ppm to 0.20 ppm, the sensitivity of the detection sensor of the prior art to the formaldehyde is 26 to 61%. However, the detection sensor of the prior art has a sensitivity of 68% to the concentration of 1 ppm of ethanol, which is rather higher than the sensitivity to the formaldehyde.

As a result, the detection sensor of the prior art has a greater response or sensitivity to ethanol when a nickel compound is included in a sensing material, so it can be seen that when formaldehyde and ethanol are present in the air or indoors, the sensing layer cannot distinguish the formaldehyde and the ethanol from each other. It can be understood that this is because, in the case of nickel, the molecular structures of an oxide and the diameter of an atom do not specifically react only to formaldehyde, but react more strongly to gases composed of organic compounds having other functional groups.

For example, it can be understood that nickel reacts more easily, strongly, and rapidly to ethanol than to formaldehyde. Accordingly, when an oxide of an alkali metal element or an oxide of an alkaline earth metal element is used in the sensing layer 300 of the gas sensor 10 of the present disclosure, nickel and a nickel oxide can be excluded.

Figure 4A:
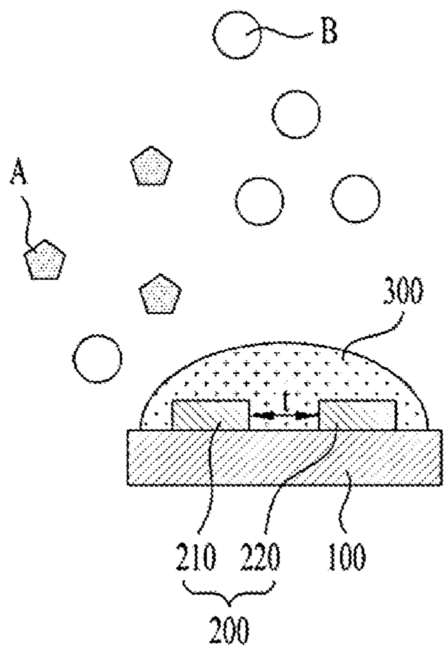
FIGS. 4A and 4B are views illustrating gas detection performed by the gas sensor of the present disclosure.
Figure 4B:
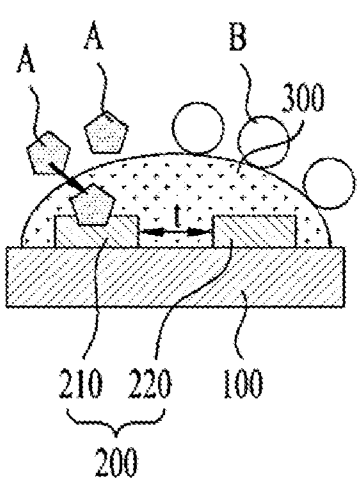

FIGS. 4A and 4B illustrate a mechanism by which the gas sensor 10 of the present disclosure specifically reacts to formaldehyde. In metal oxides, metal ions and non-metal ions combine to form a non-stoichiometric composition from a stoichiometric composition. Lattice defects accompanied in a process in which metal ions and oxide ions form a non-stoichiometric composition from a stoichiometric composition act as a donor or an acceptor.

When a material of which the sensing layer 300 of the gas sensor 10 of the present disclosure is made is the compound of $SnO_2$ with an oxide of an alkali metal or alkaline earth metal other than nickel, the formaldehyde or a formaldehyde reactor can be introduced into the lattice structure of the sensing layer 300.

The following description will be made with reference to FIG. 4A. Volatile organic compounds including formaldehyde A can exist indoors or in the air. For example, formaldehyde A and the ethanol B can coexist indoors or in the air.

FIG. 4B illustrates that formaldehyde A is accommodated in the lattice structure of the sensing layer 300. In this way, when formaldehyde A is accommodated in the lattice structure of the sensing layer 300, the capacitance or electrical resistance of the entire sensing layer 300 can be changed.

In addition, formaldehyde A accommodated in the sensing layer 300 can generate the movement of a large amount of electrons while strongly generating oxidation-reduction reactions with alkali metals or alkaline earth metals. Accordingly, the movement of a large amount of electrons generated inside the sensing layer 300 can be amplified and the electrons can be transferred to the electrode 200, and this can change the capacitance or electrical resistance of the electrode 200.

Accordingly, the gas sensor 10 of the present disclosure can detect even small amounts of formaldehyde A with high sensitivity. However, volatile organic compounds having large molecular structures or other functional groups such as the ethanol B or toluene C other than formaldehyde A cannot be introduced into the lattice structure of the sensing layer 300.

In other words, although ethanol B can contact the sensing layer 300, the ethanol B cannot be introduced into the lattice structure of the inside of the sensing layer 300. Furthermore, the ethanol B cannot cause a strong redox reaction with the sensing layer 300.

Accordingly, a volatile organic compound such as ethanol B cannot generate the movement of a large amount of electrons in the sensing layer 300 and cannot change the capacitance or electrical resistance of the sensing layer 300.

As a result, the gas sensor 10 of the present disclosure does not respond to or can have a very low sensitivity to volatile organic compounds except for formaldehyde. Accordingly, the gas sensor 10 of the present disclosure can secure high sensitivity and detection specificity to formaldehyde A.

Meanwhile, as a result of an experiment, it can be seen that the gas sensor 10 of the present disclosure requires that the electrode 200 be made of or include an indium tin oxide (ITO) so that the above-mentioned effect appears or becomes larger. This means that when the electrode 200 is made of or include a general compound of gold (Au) or platinum (Pt), the reception sensitivity of the specific capacitance change or electron movement occurring in the sensing layer 300 can be reduced.

Specifically, the electrode 200 can be made of or include a metal oxide including at least one element of Ti, Zn, In, and Sn, and does not include gold (Au) or platinum (Pt).

The sensing layer 300 can be formed to completely cover the electrode 200. In this way, the first electrode 210 and the second electrode 220 can be securely connected to each other by the sensing layer 300.

In addition, the sensing layer 300 can further improve the performance of detecting formaldehyde by maximizing an area of the sensing layer 300 exposed to atmospheric or indoor air.

Figure 5:
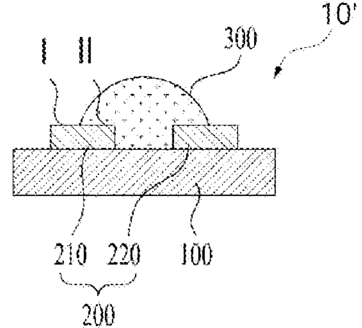
FIG. 5 is a schematic cross-sectional view illustrating another embodiment of the gas sensor of the present disclosure.

FIG. 5 illustrates another embodiment of the gas sensor 10' of the present disclosure. In the gas sensor 10' according to the embodiment, the sensing layer 300 has a property that reacts specifically to formaldehyde, so the sensing layer 300 may not be required to cover the entirety of the electrode 200.

Accordingly, in the gas sensor 10' according to the embodiment, a portion I of a surface area of the electrode 200 can be exposed to the outside, and a remaining area II thereof can be covered by the sensing layer 300. The exposed part of the electrode 200 can be referred to as the exposed area I, and the area covered by the sensing layer 300 can be referred to as the blocked area II.

In this embodiment, it is considered that the sensing layer 300 can function properly as long as the sensing layer 300 can contact formaldehyde in the air or indoors while connecting the first electrode 210 and the second electrode 220 to each other. In this way, since the sensing layer 300 can be formed in a relatively narrow area, the amount of a material of which the sensing layer 300 is formed can be minimized.

In addition, by placing the exposed area I, it is possible to easily check whether the electrode 200 is properly installed and whether the electrode 200 is operating normally. For reference, as in this embodiment, when the electrode 200 has the exposed area I, the exposed area I can be used as a part to which a lead wire for connection to the outside is connected, so the size of the gas sensor 10' can be miniaturized.

Figure 6:
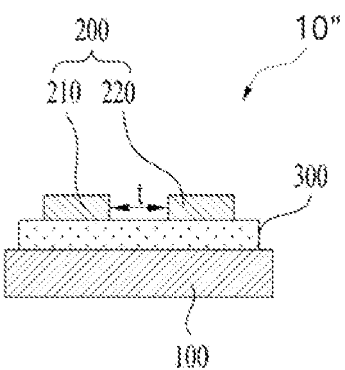
FIG. 6 is a schematic cross-sectional view illustrating still another embodiment of the gas sensor of the present disclosure.

FIG. 6 illustrates still another embodiment of the gas sensor 10" of the present disclosure. In the gas sensor 10" according to the embodiment, the sensing layer 300 has a property that reacts specifically to formaldehyde A, and thus as long as the electrodes of the electrode 200 can be connected to each other by the sensing layer 300, the sensing layer 300 can function properly at any place at which the sensing layer 300 is located.

In the embodiment, the sensing layer 300 can be formed on the substrate 100, and the electrode 200 can be formed on the sensing layer 300. The electrode 200 can be formed as one pair of the first electrode 210 and the second electrode 220 spaced apart from each other by a predetermined distance t. Here, each of the first electrode 210 and the second electrode 220 can be connected to the outside by a separate lead wire.

In addition, the electrode 200 does not react to formaldehyde A or volatile organic compounds, so the electrode 200 can be exposed indoors or to the atmosphere. In consideration of this point, the electrode 200 can be formed on the sensing layer 300.

In the embodiment, the sensing layer 300 can be first formed on the substrate 100, and the electrode 200 can be formed on the sensing layer 300. For example, the sensing layer 300 can be located between the substrate 100 and the electrode 200, and the first electrode 210 and the second electrode 220 can be formed on the surface of the sensing layer 300. Accordingly, the first electrode 210 and the second electrode 220 can be formed on the sensing layer 300, and thus it can be guaranteed that the first electrode 210 and the second electrode 220 are connected to each other by the sensing layer 300.

In the embodiment, except for surfaces on which the first electrode 210 and the second electrode 220 are seated on the sensing layer 300, all outer surfaces of the first electrode 210 and the second electrode 220 can be exposed to the outside. Accordingly, it can be easier to connect a lead wire for electrical connection with the outside. Particularly, the formation of the first electrode 210 and the second electrode 220 can be relatively easy in a manufacturing process thereof, and, after the manufacturing, maintenance thereof can be relatively easy.

Figure 7:
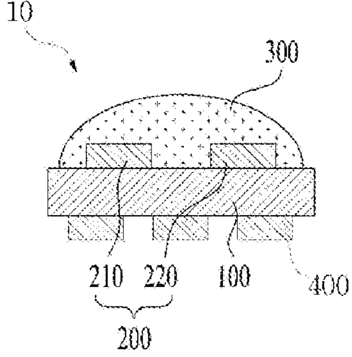
FIG. 7 is a schematic cross-sectional view illustrating that a heater is added to the gas sensor in the embodiment illustrated in FIG. 2.

Next, FIG. 7 illustrates that a heater 400 is added in the embodiment illustrated in FIG. 2. Here, for convenience of explanation, the same reference numerals as in the embodiment illustrated in FIG. 2 are used, and the heater 400 is added.

The heater 400 can provide heat to the gas sensor 10 so that the gas sensor 10 can operate at a specific temperature. The heater 400 can be made of, or include gold or platinum. As illustrated in FIG. 7, the heater 400 can be located on a surface opposite to the surface of the substrate 100 on which the electrode 200 is located. However, heaters 400 can be located around the electrode 200 on the surface on which the electrode 200 is located so as to surround the electrode 200.

Hereinafter, one embodiment of the manufacturing method of the gas sensor 10 of the present disclosure will be described. For convenience of explanation, the manufacturing method will be described based on the gas sensor 10 illustrated in FIG. 2.

In the gas sensor 10 of the present disclosure, as the material of the electrode 200, an indium tin oxide (ITO) can be used. As the material of the sensing layer 300, a tin oxide including Mg (Mg—$SnO_2$) can be used.

The manufacturing of Mg—$SnO_2$ will be described. Tin chloride ($SnCl_2$) is reacted with an aqueous solution of magnesium sulfate. Here, the ratio of the contents of Sn and Mg can be preset to be Sn:Mg=20:1 in terms of a molar ratio. A precipitate can be obtained by dropping aqueous ammonia into this aqueous solution.

This precipitate can be washed with distilled water and then dried. The drying can be done in the air. Mg—$SnO_2$ can be obtained by calcining the dried powder at 600 to 800° C.

The electrode 200 made of or including an indium tin oxide (ITO) can be formed on the surface of the substrate 100. After forming the first electrode 210 and the second electrode 220 of the electrode 200 on the substrate 100, the sensing layer 300 can be formed. The sensing layer 300 can use the above-described Mg—$SnO_2$ as a material. The sensing layer 300 can be formed by dispersing and applying Mg—$SnO_2$ onto a mixed solution of pure water and glycerin to connect the first electrode 210 and the second electrode 220 to each other.

After forming the sensing layer 300, the sensing layer 300 can be heated at 500° C.

The measuring of response to gas by using the gas sensor 10 of the present disclosure will be described. The gas sensor 10 can be installed in a gas introduction container and exposed to gas whose concentration is adjusted. In this state, the sensitivity of the gas sensor 10 to the gas can be measured by detecting the change of a resistance value between the first electrode 210 and the second electrode 220.

By using pure air as a dilution gas, concentration-adjusted gas can be generated by a permeator and a flow rate thereof can be adjusted by a mass flow controller so that the gas can be introduced into the gas introduction container. Humidity can be generated by bubbling distilled water. Relative humidity obtained as the result of FIG. 3 can be preset to be 54%.

In the gas sensor 10, a resistance value can be obtained by applying voltage through wiring installed in the sensor element of an electrometer and measuring an electric current.

The gas sensor 10 of the present disclosure can be used in a variety of home appliances. For example, the gas sensor 10 can be installed in an air conditioner, an air purifier, a washing machine, a dryer, and a clothing management device to detect whether formaldehyde is generated and to perform necessary operations accordingly.

Since the present disclosure can be implemented by being modified in various forms, the scope of rights thereof is not limited to the above-described embodiments. Therefore, if a modified embodiment includes the components of the claims of the present disclosure, the embodiment should be regarded as belonging to the scope of the present disclosure.

What is claimed is:

1. A gas sensor for detecting volatile organic compounds, the gas sensor comprising:
- a substrate including a non-conductive material;
- at least one pair of electrodes located on the substrate and including a conductive material, the at least one pair of electrodes being electrically connected to an outside; and
- a sensing layer configured to be in contact with at least a portion of the at least one pair of electrodes or to cover the at least one pair of electrodes, the sensing layer reacting to a formaldehyde, wherein the sensing layer comprises Mg—$SnO_2$.

2. The gas sensor of claim 1, wherein the at least one pair of electrodes include indium tin oxide (ITO).

3. The gas sensor of claim 1, wherein the at least one pair of electrodes comprise a first electrode formed on the substrate, and a second electrode formed on the substrate by being spaced apart from the first electrode, and wherein the sensing layer is disposed to connect the first electrode with the second electrode.

4. The gas sensor of claim 3, wherein the sensing layer is configured to expose at least a portion of each of the first electrode and the second electrode to air.

5. The gas sensor of claim 1, wherein a heater is provided on the substrate, the heater being located on a surface of the substrate on which the at least one pair of electrodes are located or on a surface opposite to the surface of the substrate on which the at least one pair of electrodes are located.

6. The gas sensor of claim 1, wherein the sensing layer has a curved outer surface.

7. The gas sensor of claim 1, wherein the formaldehyde is incorporated into a lattice structure of the sensing layer, and wherein at least one of ethanol and toluene is not incorporated into the lattice structure of the sensing layer.

8. A gas sensor for detecting volatile organic compounds, the gas sensor comprising:

a substrate including a non-conductive material;

a sensing layer located on the substrate, the sensing layer reacting to formaldehyde, and the sensing layer being made of Mg—$Sno_2$; and at least one pair of electrodes including a conductive material and configured to detect electron movement and capacitance inside the sensing layer, the at least one pair of electrodes being electrically connected to an outside, wherein the at least one pair of electrodes comprise a first electrode including a conductive material, and a second electrode configured to supply conduct an electric current to the first electrode or to conduct an electric current from the first electrode, and wherein the sensing layer connects the first electrode with the second electrode and is configured to expose at least a portion of each of the first electrode and the second electrode to air.

9. The gas sensor of claim 8, wherein the sensing layer is disposed between the substrate, and the first electrode and the second electrode.

10. The gas sensor of claim 9, wherein the first electrode and the second electrode are provided on an outer surface of the sensing layer.

11. The gas sensor of claim 10, wherein the sensing layer is rectangular in shape.

12. The gas sensor of claim 8, wherein the sensing layer shields a portion of the first electrode and a portion of the second electrode.

13. The gas sensor of claim 8, wherein a heater is provided on the substrate, the heater being located on a surface of the substrate on which the at least one pair of electrodes are located or on a surface opposite to the surface of the substrate on which the at least one pair of electrodes are located.

14. A method for manufacturing a gas sensor for detecting volatile organic compounds, with the gas sensor having a sensing layer configured to connect electrodes to each other formed on a substrate, the method comprising:

forming the electrodes using indium tin oxide (ITO), and forming the sensing layer by using Mg—$SnO_2$, wherein the sensing layer is formed by dispersing and applying the Mg—$SnO_2$ onto a mixed solution of pure water and glycerin and heating the mixed solution, onto which the Mg—$SnO_2$ is applied, to a predetermined temperature.

15. The method of claim 14, wherein forming of the sensing layer forms the sensing layer between the substrate and the electrodes.

16. The method of claim 14, wherein forming of the electrodes forms the electrodes between the substrate and the sensing layer.

* * * * *